United States Patent [19]

Bonello et al.

[11] Patent Number: 4,732,163
[45] Date of Patent: Mar. 22, 1988

[54] REMOTE CONTROLLED GUIDE FOR A CATHETER

[75] Inventors: Philippe Bonello, Grand-Saconnex; Maurice Jeanmonod, Meyrin, both of Switzerland

[73] Assignee: Sarcem S.A., Meyrin, Switzerland

[21] Appl. No.: 929,081

[22] Filed: Nov. 10, 1986

[30] Foreign Application Priority Data

Nov. 21, 1985 [CH] Switzerland .............. 04962/85

[51] Int. Cl.$^4$ .............................................. A61B 5/00
[52] U.S. Cl. ................................... 128/772; 604/95; 604/280
[58] Field of Search .............. 128/772, 656–658; 604/95, 110, 164, 171, 264, 280, 282, 170, 283

[56] References Cited

U.S. PATENT DOCUMENTS

| 3,521,620 | 7/1970 | Cook ........................ 604/95 |
| 3,786,810 | 1/1974 | Pannier, Jr. et al. . |
| 3,789,841 | 2/1974 | Antoshkiw . |
| 3,854,473 | 12/1974 | Matsao ..................... 128/772 |
| 3,913,565 | 10/1975 | Kawakara ................ 128/772 |
| 4,000,739 | 1/1977 | Stevens .................... 604/280 |
| 4,215,703 | 8/1980 | Willson ................... 128/772 |
| 4,430,083 | 2/1984 | Ganz et al. ............. 128/772 |
| 4,456,017 | 6/1984 | Miles ....................... 128/772 |
| 4,543,090 | 9/1985 | McCoy ..................... 604/95 |
| 4,548,206 | 10/1985 | Osborne .................. 128/772 |
| 4,554,929 | 11/1985 | Samson et al. ......... 128/772 |
| 4,559,046 | 12/1985 | Grosberg et al. ...... 128/772 |
| 4,643,194 | 2/1987 | Fogarty ................... 128/772 |

FOREIGN PATENT DOCUMENTS 4327695 11/1968 Japan ........................ 604/95

Primary Examiner—Max Hindenburg
Attorney, Agent, or Firm—Young & Thompson

[57] ABSTRACT

A remote controlled guide for a catheter, characterized by the fact that its end called the head which is formed of a cylindrical coil spring (2) having separated coils is mounted coaxially at the end of a tube (1) and can be bent at will so as to facilitate its introduction and then its passage through the blood vessels. To do that, the user acts axially on the rear end of a flexible pulling member (5) the other end of which is fastened to the upper portion of the head at a point which is eccentric with the axis of said latter, this flexible pulling member (5) passing through the tube (1). Furthermore, and in order to inject at the level of the head a contrast liquid inside the blood vessel, the rear end of the tube (1) is removably fixed in a tight manner onto a frame member (6) provided with a lateral channel (17) communicating with the tube (1), the liquid being able to escape through the coils of the spring (2). When the guide for the catheter is set place, the frame member (6) is disconnected from the tube (1) to be replaced by an extension (15) having a stud (16). Now, the guide for the catheter is in its working state to support and guide a catheter having an inflatable balloon.

5 Claims, 2 Drawing Figures

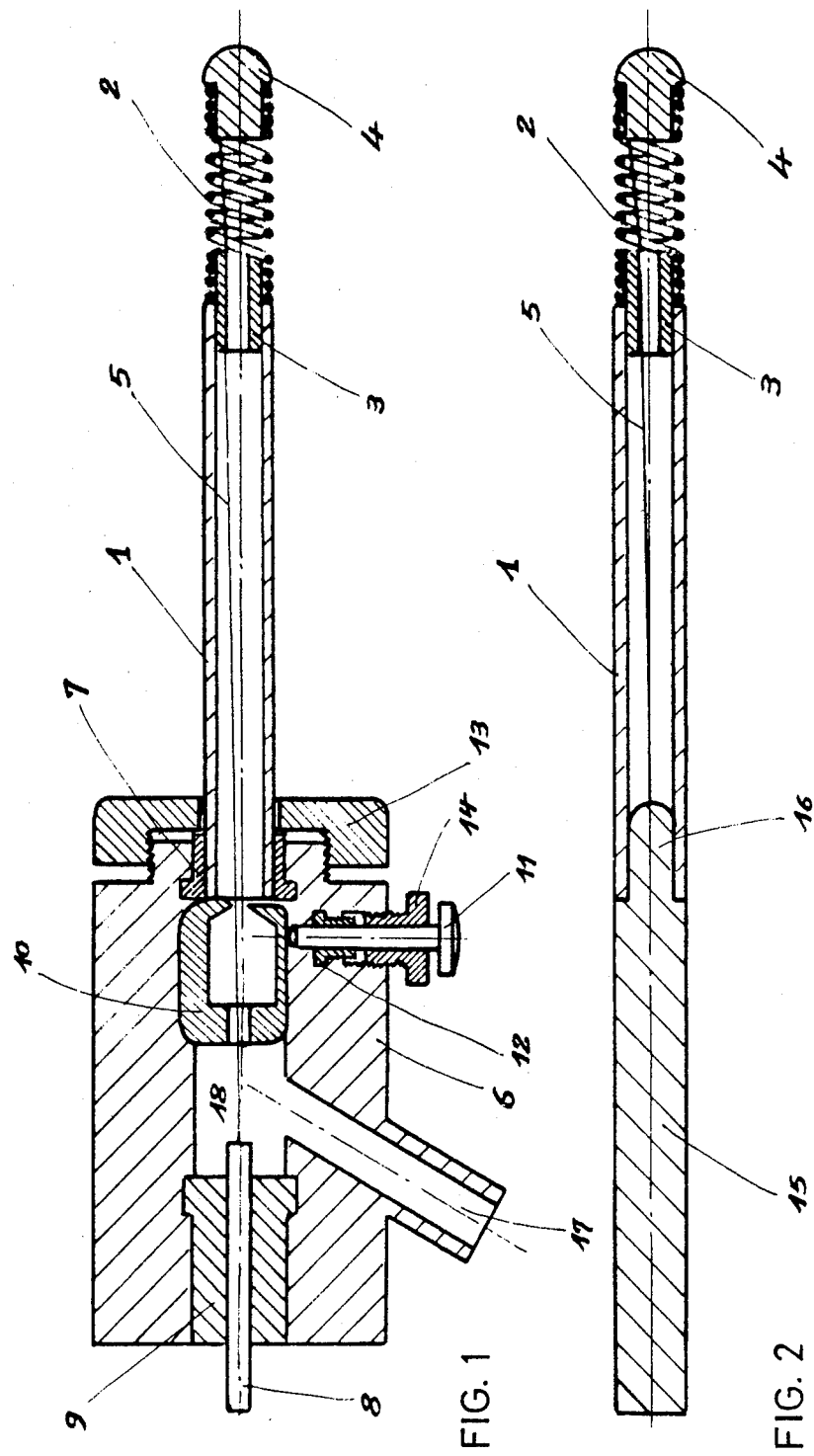

REMOTE CONTROLLED GUIDE FOR A CATHETER

The present invention has for its object a remote controlled guide for a catheter for insertion into coronary vessels.

The treatment of the narrowing of the arterial vessels is current performed by dilation by means of an instrument called a catheter having an inflatable balloon, and it is difficult to place the said balloon inside the stenosis, an operation which is of course the more difficult, the more important the narrowing is.

In order to simplify this manipulation which consists thus to place the inflatable balloon at the right place, a kind of metallic rod called a guide for catheter, having a very thin calibre and the end of which is slightly bent, is first introduced in the vessels, then passed through the stenosis and remains in place in its position and thus defines a path for the inflatable catheter intended to be pushed along this guide for the catheter until each of the narrowing zones is reached.

If such a method is applied in very numerous cases, it presents however the drawback of using a guide for a catheter the bending of the extremity of which cannot be modified as a function of the successive variable directions which said latter has to take in order to pass the multiple ramifications. The present invention has precisely for its object a guide for a catheter the bending of the extremity of which can be modified by remote control and this at any time during the setting in place of said guide for catheter.

FIG. 1 shows a cross-section of the guide for the catheter such as it presents during all the time for its setting in place.

FIG. 2 shows, after having being set in place, the guide for the catheter modified with its elongation.

The remote controlled guide for a catheter shown in the drawing comprises a tube 1 at the end of which is mounted coaxially the head of the catheter guide, formed of a cylindrical coil spring 2, the base of which is fitted onto a pierced piece 3 itself driven within the tube 1, of an end piece 4 the rod of which is fitted onto the other end of the cylindrical coil spring 2, and of a flexible pulling member 5 the fixing point of which to the end piece 4 is eccentric with respect to the axis of said end piece. On the other hand a frame element 6 is fixed in a tight manner by means of o-ring 7 and in a removable manner onto the tube 1, a portion in part cylindrical 8 to which is fixed the flexible pulling member 5, a bushing 9 ensuring the tightness between the frame element 6 and the cylindrical portion 8, a cutter 10, a pusher member 11 tight with the frame member 6 by means of an o-ring 12, a threaded element 13, a threaded element 14, an extension 15 with its stud 16.

At the start and before any chirurgical intervention, caution has to be taken that the two threaded elements 13 and 14 are well tightened to ensure the tightness of the frame element 6 with the tube 1 on the one side, and with the push button 11 on the other side so that the o-rings 7 and 12 are compressed. Thereafter and in order to guide the head of the guide for a catheter such as it is presented in FIG. 1 into the origin of one or another vessel and then within the zones to be treated, the user has therefore three degrees of liberty that is to go forward and backward with the whole assembly and consequently with the head, the rotation of the whole assembly on itself in one direction or the other with respect to its axis, and the inclination of the head only or the straightening of this head, these two latter functions being possible thanks to the pulling force backwardly against the resilient action of the cylindrical coil spring 2 or forwardly that the user can impose on the cylindrical portion 8 and therefore on the flexible pulling member 5 housed within the tube 1, the cylindrical part 8 being directly seizable manually through its rear end or attached by the same end to a classical mechanism not shown on the drawing for example of the micrometric type.

Then can be performed the classical and well known function of introducing contrast liquid within the vessel in order to trace for a radioscopic examination. For that, the contrast liquid is injected through the channel 17 of the frame element 6 filling the chamber 18 and then the tube 1 and escaping within the blood vessel through the spaced coils of the cylindrical coil spring 2.

When the guide for a catheter is definitively in place, the user will unscrew the screwed element 14 liberating thus the axis of the push button 11 from the o-ring 12 and pushes then this push button 11 thereby displacing the jaws of the cutter 10 the one toward the outer and cutting the flexible pulling element 5, thereafter the threaded element 13 will be totaly unscrewed freeing the tube 1 which will be separated from the frame element 6. In this state, it is possible to replace the frame element 6 with the elongation 15 by driving its stud 16 firmly into the rear portion of the tube 1.

We claim:

1. A remote controlled guide for a catheter, comprising a tube terminating at one end in a hollow flexible finger formed in part by a coil spring, a flexible pulling element that is secured to the finger eccentrically of the coil spring and that extends through the tube, the other end of the tube being removably secured to a frame element containing a control device for pulling the flexible member thereby to bend the finger relative to the tube, and a cutter carried by the frame element for selectively cutting the flexible pulling member thereby to permit separation of the frame element from the tube.

2. Apparatus as claimed in claim 1, said finger including an end piece and said coil spring interconnecting said end piece and said one end of the tube.

3. Apparatus as claimed in claim 1, the frame member having a lateral channel communicating with the inside of the tube for injecting a liquid through the tube.

4. Apparatus as claimed in claim 1, and a push button on the frame element for actuating said cutter to cut the flexible pulling member.

5. Apparatus as claimed in claim 1, and a member insertable in said other end of the tube and constituting a prolongation of the tube for closing the tube when said frame element is disconnected from the tube.

* * * * *